(12) United States Patent
de Juan, Jr. et al.

(10) Patent No.: US 6,309,419 B1
(45) Date of Patent: Oct. 30, 2001

(54) TYMPANIC MEMBRANE PROSTHESIS WITH MECHANICAL FIXATION

(75) Inventors: Eugene de Juan, Jr., Phoenix, MD (US); R. Scott Rader, Guilford, CT (US); Terry H. Shelley, Hampstead, MD (US); Andrew N. Lamborne, Denver, CO (US); Alexander C. Walsh, Hunt Valley; John K. Niparko, Glenarm, both of MD (US)

(73) Assignee: Johns Hopkins University, Balimtore, MD (US)

( * ) Notice: Subject to any disclaimer, the term of this patent is extended or adjusted under 35 U.S.C. 154(b) by 0 days.

(21) Appl. No.: 09/276,710

(22) Filed: Mar. 26, 1999

(51) Int. Cl.$^7$ ........................................ A61F 2/18
(52) U.S. Cl. ................................................ 623/10
(58) Field of Search .................. 623/4.1, 6.63, 623/10; 606/215, 233

(56) References Cited

U.S. PATENT DOCUMENTS

| | | | |
|---|---|---|---|
| 3,196,462 | * | 7/1965 | Robinson ................................ 623/10 |
| 3,825,009 | * | 7/1974 | Williams ................................ 623/10 |
| 4,601,723 | * | 7/1986 | McGrew ................................ 623/10 |
| 4,641,651 | * | 2/1987 | Card ...................................... 623/10 |
| 4,704,126 | * | 11/1987 | Baswell ................................. 623/10 |
| 4,712,550 | | 12/1987 | Sinnett . |
| 4,740,209 | * | 4/1988 | Gersdorff .............................. 623/10 |
| 4,784,138 | | 11/1988 | Sinnett . |
| 5,236,455 | | 8/1993 | Wilk et al. . |
| 5,501,700 | | 3/1996 | Hirata . |

OTHER PUBLICATIONS de Juan, Jr. et al., "Retinal Tacks", American Journal of Ophthalmology, vol. 99, No. 3, Mar. 15, 1985, pp. 272–274.
de Juan, Jr. et al., "Mechanical Retinal Fixation Using Tacks", Ophthalmology, vol. 94, No. 4, Apr. 4, 1987, pp. 337–340.

* cited by examiner

Primary Examiner—Michael J. Milano
(74) Attorney, Agent, or Firm—Pillsbury Winthrop LLP

(57) ABSTRACT

A tympanic membrane prosthesis is provided that includes, in combination, a generally flat, planar membrane sized to overlay a tear or perforation in the tympanic membrane and having at least one preformed perforation, and at least one mechanical fixation device for fixing the membrane to the tympanic membrane of a patient. Each mechanical fixation device is a tack component including a sharp, piercing distal end, an enlarged proximal end and a shaft extending therebetween. A tack insertion device is provided to guide the tack to and through the tear covering membrane.

12 Claims, 3 Drawing Sheets

TYMPANIC MEMBRANE PROSTHESIS WITH MECHANICAL FIXATION

BACKGROUND OF THE INVENTION

1. Field of the Invention

The present invention relates to a tympanic membrane prosthesis and in particular to the mechanical fixation of a synthetic prosthesis to the tympanic membrane to act as a substrate or stimulant for cell growth and healing.

2. Description of the Related Art

The tympanic membrane or as it is often referred to, the eardrum, is the layer of tissue that separates the outer ear canal from the middle ear. The middle ear contains the bones responsible for conducting or transmitting sounds to the inner ear and then on to the brain. The tympanic membrane is responsible for receiving sound pressure waves and transmitting them to the bony apparatus inside the middle ear. The tympanic membrane is typically located more than 20 mm inside the ear canal but can be visualized by spreading the soft outer portion of the canal with a speculum and looking through either a hand held otoscope or through a larger oto-microscope.

The tympanic membrane can be perforated as a result of a variety of different processes such as infections of the middle ear, direct trauma or poor post-operative healing. While perforations of the tympanic membrane do not present an immediate danger to the patients hearing apparatus, they can lead to decreased hearing, autophony (hearing an echo of ones own speech), or pain secondary to infection. Tympanic membrane perforations can be subcategorized based on the duration of the perforation, i.e., acute verses chronic, and the presence or absence of drainage i.e., dry verses wet. These subcategories have an effect on a prognosis of a given perforation. For example, acute dry perforations such as those resulting from a direct trauma to the eardrum from a sharp instrument often or usually heal spontaneously. On the other hand, patients with acute or chronic otitis media can develop chronic perforations having a duration of longer than two months that can remain unhealed for periods longer than a decade. The relatively common use of pressure equalization tubes in children with recurrent otitis media has also resulted in an increase in chronic perforations in these young patients.

In response to this pervasive problem, many techniques have been developed for the closure of tympanic membrane perforations. Myringoplasty is a procedure wherein the eardrum is patched with a graft material, such as muscle fascia. It has a success rate that often exceeds 95% but involves the use of an operating room, anesthesia and an incision to harvest the graft material. These factors not only expose the patient to risks of infection, bleeding, anesthesia, hearing loss, etc., but also result in high medical costs. Non-surgical techniques, on the other hand, can provide the benefit of decreased risk and discomfort for the patient as well as decreased cost. Thus, many non-surgical approaches to the healing of tympanic membrane perforations have been developed including rice-paper patches and growth stimulants applied to the perforation periphery. Such techniques, however, have met with only limited success and studies of their efficacy have been conducted mostly in animal models or in small numbers of human patients in uncontrolled studies in Europe. Thus, their efficacy remains unclear.

SUMMARY OF THE INVENTION

It is an object of the present invention to provide an alternative to the invasive surgical technique referenced above for the healing of tympanic membrane perforations.

To achieve the foregoing and other objects, the present invention relates to the mechanical fixation of a synthetic prosthesis to the tympanic membrane to act as a substrate or stimulant for cell growth and healing. More particularly, in accordance with the present invention, a tympanic membrane prosthesis is provided that comprises, in combination, a generally flat, planar membrane sized to overlay a tear or perforation in the tympanic membrane and having at least one preformed perforation, and at least one mechanical fixation device for fixing the membrane to the tympanic membrane of a patient. Each mechanical fixation device is a tack component including a sharp, piercing distal end, an enlarged proximal end and a shaft extending therebetween.

These and other objects and advantages of the present invention will become clearer after careful consideration is given to the following detailed description of the preferred exemplary embodiments thereof.

BRIEF DESCRIPTION OF THE DRAWINGS

Reference will hereinafter be made to the accompanying drawings wherein like reference numerals throughout the various figures denote like structural elements, and wherein.

DETAILED DESCRIPTION OF THE PRESENTLY PREFERRED EXEMPLARY EMBODIMENTS

Figure 2:
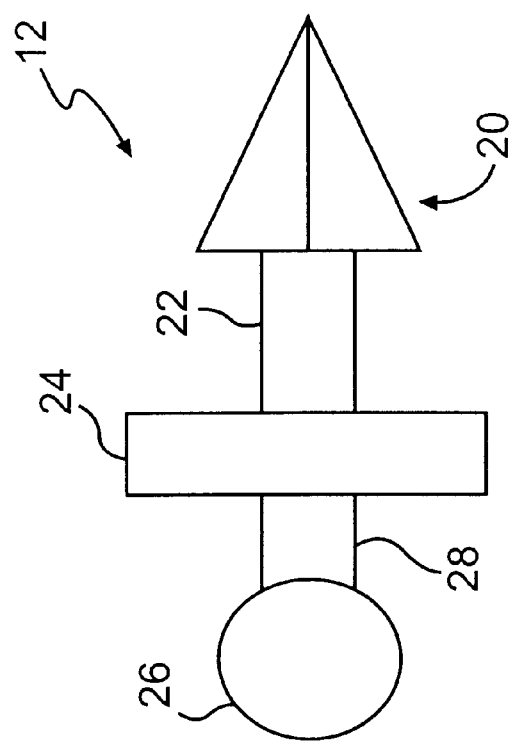
FIG. 2 is an elevational view of a fixation tack provided in accordance with an exemplary embodiment of the invention.

In accordance with the present invention, a tympanic membrane prosthesis 10 is provided to promote healing of non-spontaneously healing tympanic membrane perforations. In accordance with the present invention, the tympanic membrane prosthesis can be applied in a simple outpatient procedure that may effectively provide for healing of a tympanic membrane perforation and thus avoid the need for a Myringoplasty procedure in many cases.

The invention may be characterized as a combination of a membrane prosthesis 10 and at least one fixation component 12, or as a three component system, which further includes a delivery instrument 14. More particularly, the first component of the inventive system is the tympanic membrane prosthesis 10, illustrated by way of example in the plan view of FIG. 1, which is disposed over the perforation and provides a substrate for endothelial cell growth. The second component of the inventive system is the fixation component, which in the illustrated embodiment is at least one and typically a plurality of fixation tacks 12 for securing the membrane prosthesis 10 to the tympanic membrane. The third component of the system provided in accordance with the invention is a manually operable tack insertion device 14.

Figure 1:
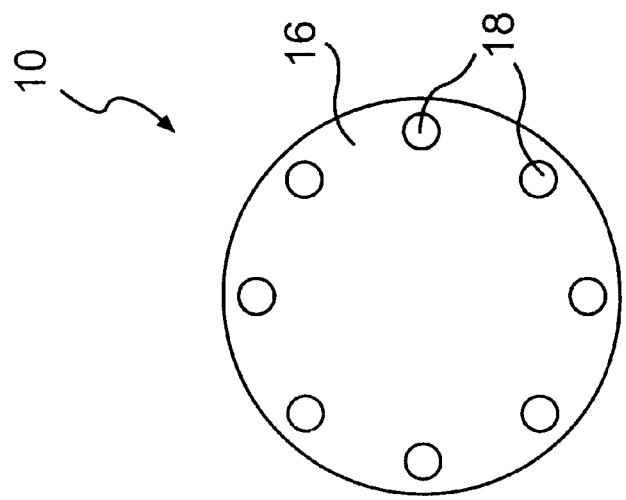
FIG. 1 is a plan view of a tympanic membrane prosthesis provided in accordance with the present invention.

With reference to FIG. 1, the artificial membrane provided in accordance with the presently preferred embodiment of the invention as a substrate to overly the tympanic membrane perforation is a thin disc, on the order of about 4 to 6 mm (about 0.157–0.236 inches) in diameter. In the presently proposed embodiment, the thin disc is TEFLON® (PTFE).

However, other biocompatible polymers may be used, as will be apparent to the skilled artisan from the environment and intended use thereof. In the illustrated embodiment, the prosthesis 10 comprises a disc 16 having a plurality of holes 18 are defined adjacent and about the perimeter thereof, at least one of which receives a fixation tack 12 to secure the membrane or disc 16 at the periphery of the respective tear. In the illustrated embodiment, a plurality of peripheral apertures are provided, pre-defined in the patch. However, only one, two or three small fixation tacks will be ultimately required to suitably retain the patch in place. These PTFE or like substrates can be pattern stamped in production.

Figure 4:
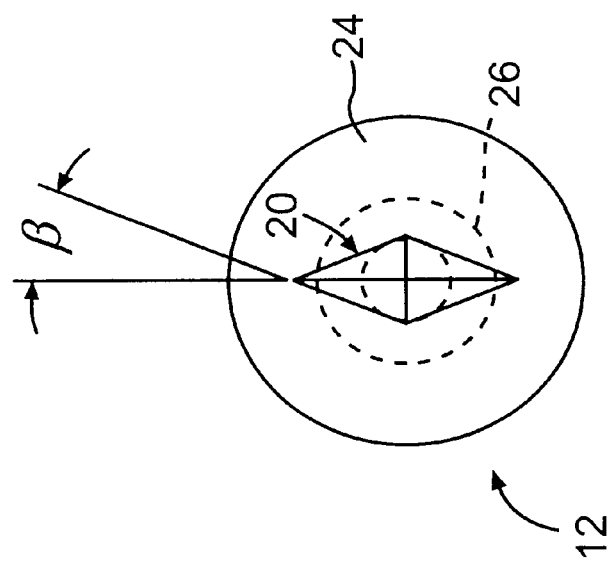
FIG. 4 is an end elevational view taken from the right of FIG. 2.
Figure 3:
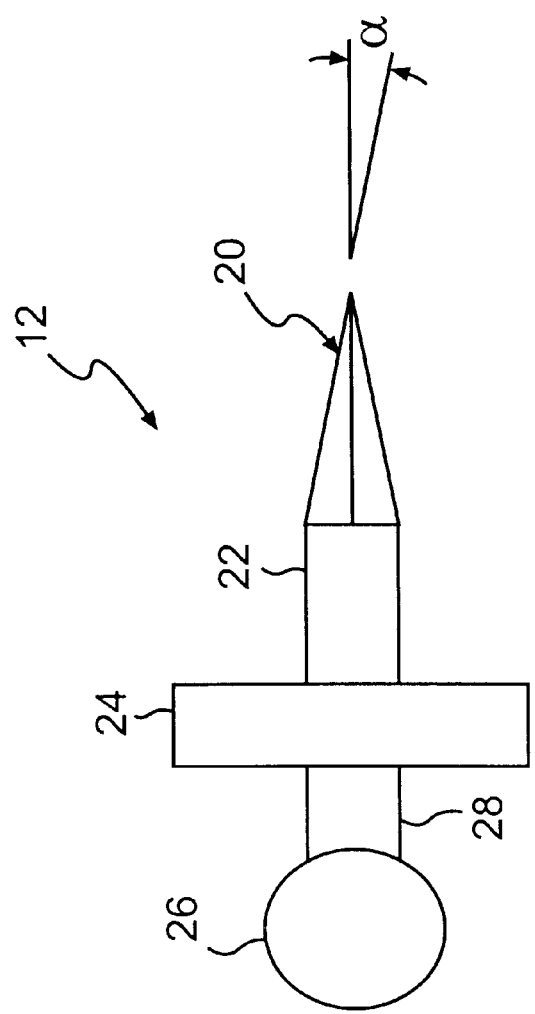
FIG. 3 is a view taken from above in FIG. 2.
Figure 5:
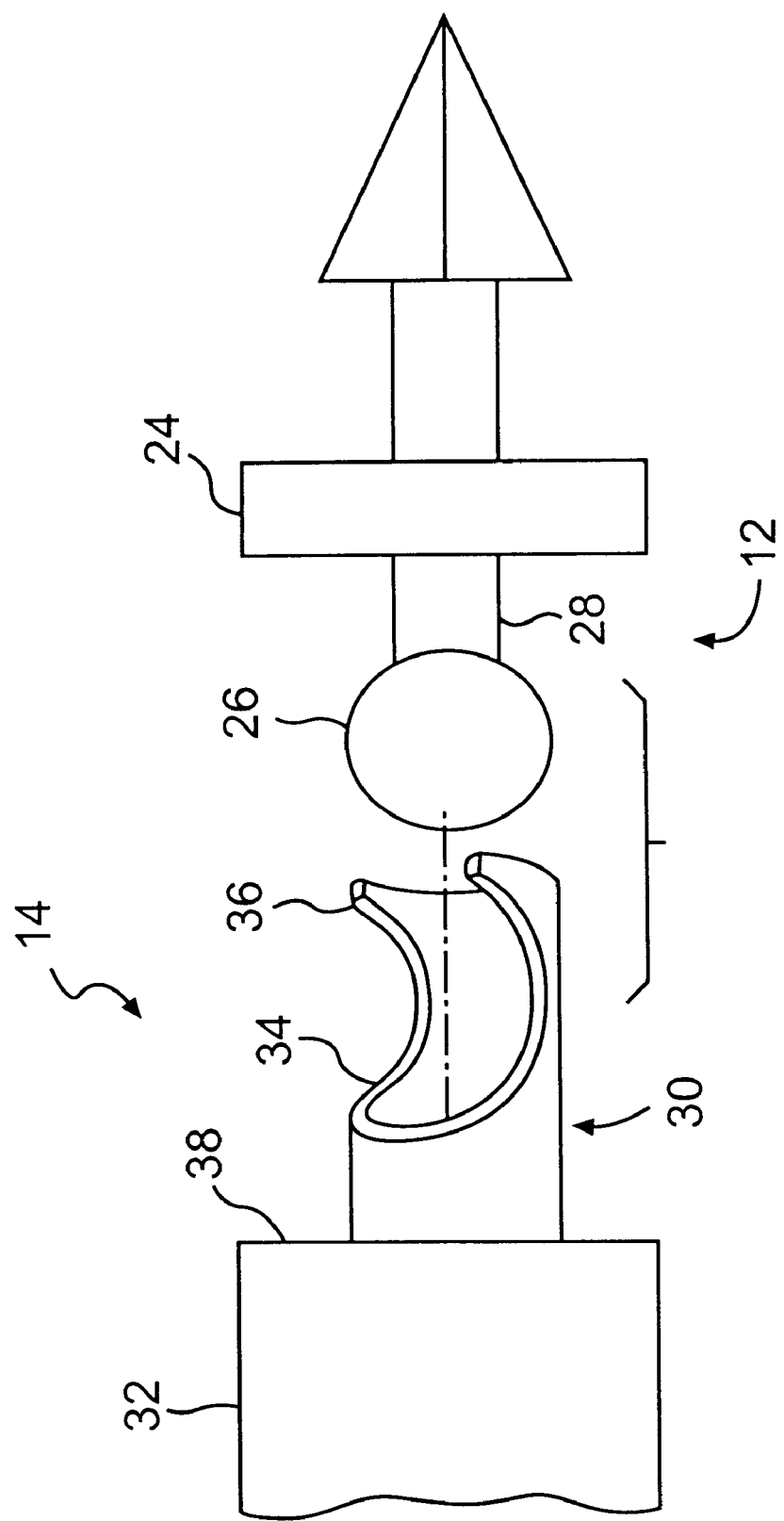
FIG. 5 is a schematic perspective view of an exemplary insertion device end adjacent a fixation tack.

The second component of the system of the invention is the fixation tack 12 shown by way of example in FIGS. 2–4. It accordance with the presently proposed embodiment, the fixation tacks are made from stainless steel. However, alternative materials include titanium, plated brass, anodized aluminum, other metal alloys, or even plastic; suitable materials being apparent to the skilled artisan from the environment and intended use thereof.

The tympanic membrane tacks 12 proposed in accordance with the present invention are made of, for example, hardened 400 series stainless steel and have a sharpened diamond point tip 20 with barbed edges ground into the distal end. In an exemplary embodiment, the grinding angle $\alpha$ of the diamond tip is on the order of about 9°–10°, and most preferably about 9.5°. Angle $\beta$, shown in FIG. 4, is on the order of about 20°–25° and in the illustrated embodiment is about 22°.

The length of the piercing head of the tack in the illustrated embodiment is about 0.030 inches (about 0.75 mm) and the diamond or arrow head 20 has a maximum transverse dimension adjacent its proximal end of about 0.025 inches (about 0.64 mm). The mid-section of the tack is a small diameter shaft 22, sized to fit the holes 18 of the substrate material 16. In the illustrated embodiment, the shaft has a diameter of about 0.010 inches (about 0.25 mm). At the proximal end of the mid-section shaft, a larger diameter stop plate 24 is provided as a positive stop during tack insertion, as explained below. The stop plate disc 24 has a diameter of about 0.040 inches (about 1 mm) and in the illustrated embodiment a thickness in the axial direction of the tack of about 0.010 inches (about 0.25 mm).

The length of the shaft 22 is sufficient to provide full penetration of the artificial membrane 16 as well as the tympanic membrane without bringing the tip of the tack too close to the structures behind the membrane, i.e., the middle ear structures. In the illustrated embodiment, the length of the mid-section shaft 22, between the piercing head proximal end and the stop plate or disc is about 0.020 inches (about 0.50 mm).

At the most proximal end of the tack, a ball shape head 26 is provided to facilitate grasping with a simple instrument from a variety of angles of approach. In the illustrated embodiment, the spherical head 26 of the tack 12 has a diameter of about 0.020 inches (about 0.50 mm) and is spaced from the stop plate or disc 24 so as to facilitate securement and detachment of the delivery instrument thereto. In the illustrated embodiment, the spherical head of the tack is offset from the stop plate disc a distance of about 0.011 inches (about 0.28 mm). Thus, the overall length of the tack is about 0.09 inches (about 2.29 mm), but that dimension may vary to a greater or lesser extent depending upon the configuration of the insertion instrument, the anticipated thickness of the tympanic membrane and the anticipated spacing of the middle ear structures from the tympanic membrane.

The insertion instrument 14 is manually operated to displace the tip of a shaped inner core 30 inwardly past the tip of a hollow outer tube 32 whereby at least a portion of the tack 12 is maintained within the hollow outer tube 32 until delivery through the perforation of the artificial membrane is to be effected. In a presently preferred embodiment, the core member is scalloped as at 34 with a disc region proximally for engaging the proximal face of the ball 26 of the tack 12 and has a narrowed section distally as at 26 to form a grip for the distal end of the ball 26, about the shank 28 extending between the ball 26 and the stop plate or disc 24.

When the core is extended, the disc region 34 engages the ball portion of the tack. When the core is retracted, the distal face 38 of the outer tube 32 engages the plate 24 of the tack to align the tack with the insert tool. The tack is thus rigidly held in this position for easy insertion and then released by extending the core again and disengaging the ball. Thus, a forked engagement with the shank 28 intermediate the ball and the disc enables a retracting force to be applied to the tack to draw it into the outer tube 32, which displacement is limited by engagement of the stop 24 with the end face 36 of the outer tube 32. The tack is advanced relative to the outer tube by advancement of the core, and coincident engagement of the disc region 34 with the tack end 26. Once the core projects beyond the outer end of the tube, the core can be disengaged from the tack shank.

By way of example, the shaft of the insertion tool 14 is approximately two inches in length and 0.05 inches in diameter. The length is provided in order to reach the tympanic membrane through the ear canal and the diameter should be as small as possible in order to permit visualization e.g. through a speculum with an operating microscope. The insertion tool is preferably attached to a suitable handle that is constructed and arranged so that squeezing the handle or a component provided thereon extends the core, inner shaft of the insertion tool, allowing release of the tack. A knurled knob may be provided at the end of the handle to rotate the tack following insertion, as described below. A suitable handle for the insertion tool, as described above, has been developed by the Johns Hopkins Microsurgery Advanced Design Laboratory.

As an alternative to the structure described above, the insertion tool or instrument may include a core having at least two pivotably mounted ball engagement arms at a distal end thereof for capturing the ball head of the respective tack. In this alternative the outer sleeve pivots the capture arms into a tack capturing orientation when the outer sleeve is advanced relative to the core or the core is retracted relative to the outer sleeve. Thus a tack may be loaded in the delivery instrument by capturing the ball end of the tack within the delivery instrument. Displacement of the outer sheath relative to the tack not only captures the ball head with the pivot arms but on engagement with the stop disc, secures the tack in place.

In either of the above described instruments indicia may be provided at the proximal end of the core and/or outer sheath for reliably indicating when the core and tack have been disposed sufficiently beyond the distal end of the outer sheath for the tack to be released, whereby the applicator can be disengaged and retracted.

To apply the prosthesis in accordance with the invention, the PTFE substrate is trimmed to size, if necessary, and placed over the affected region of the tympanic membrane. A tack is loaded into the tip of the insertion instrument which is then placed into the ear canal. The instrument can be stabilized by resting the outer cover shaft against the wall of the ear canal. The tack is positioned in a peripheral hole of the artificial membrane and pushed through the underlying tympanic membrane. At this point, the instrument may be rotated 90° to rotate the barbs of the tack head out of the plane of insertion, in order to prevent the tack from sliding back out of the insertion incision over time. Following placement, the instrument tip is actuated to release the ball shape of the tack. The barbed tip and positive stop of the tack provide positive location of both the tack and substrate.

While the invention has been described in connection with what is presently considered to be the most practical and preferred embodiments, it is to be understood that the invention is not to be limited to the disclosed embodiments, but on the contrary, is intended to cover various modifications and equivalent arrangements as will be appreciated by those of skill in the art to which it pertains.

What is claimed is:

1. A tympanic membrane prosthesis comprising, in combination:
   a generally flat, planar membrane sized to overlay a tear or perforation in a tympanic membrane, at least one preformed perforation being defined in said membrane material, adjacent an outer peripheral edge thereof;
   at least one mechanical fixation device for fixing said membrane material to a tympanic membrane of a patient, each said mechanical fixation device comprising a tack component including a sharp, piercing distal end, an enlarged proximal end and a shaft extending therebetween.

2. A tympanic membrane prosthesis as in claim 1, wherein each said tack component further comprises a stop plate extending radially from said shaft intermediate said sharp distal end and said enlarged proximal end.

3. A tympanic membrane prosthesis as in claim 1, wherein said enlarged proximal end is generally spherical in shape.

4. A tympanic membrane prosthesis as in claim 2, wherein said stop plate has a generally circular outer peripheral edge.

5. A tympanic membrane prosthesis as in claim 4, wherein said enlarged proximal end is generally spherical in shape.

6. A tympanic membrane prosthesis as in claim 5, wherein a radius of said stop plate is greater than a radius of said spherical proximal end.

7. A tympanic membrane prosthesis as in claim 1, wherein said piercing distal end is an arrow shaped tip having a first dimension in a first direction and a second dimension in a second direction disposed perpendicular with respect to said first direction, a maximum dimension of said arrow shaped tip in said first direction being greater than a diameter of said shaft.

8. A tympanic membrane prosthesis as in claim 7, wherein a maximum dimension of said arrow shaped tip in said second direction substantially corresponds to said diameter of said shaft.

9. A tympanic membrane prosthesis as in claim 1, wherein the membrane and the at least one mechanical fixation device are adapted to be inserted through an ear canal of a patient.

10. A method of mechanically fixing a synthetic prosthesis to a tympanic membrane within an ear canal comprising:
    providing an insertion instrument;
    providing a membrane component;
    providing at least one tack component for securing the membrane component to the tympanic membrane;
    said membrane component comprising:
      a generally flat, planar membrane sized to overlay a tear or perforation in the tympanic membrane, at least one performed perforation being defined in said membrane, adjacent an outer peripheral edge thereof;
    each said tack component comprising:
      a sharp, piercing distal tip, an enlarged proximal head and a shaft extending therebetween;
    the method comprising the steps of:
    inserting the membrane through the ear canal;
    disposing the membrane component adjacent a tympanic membrane of a patient;
    loading a said tack component one of on and in said insertion instrument;
    inserting said tack component with insertion instrument, through the ear canal;
    driving said tack component through said membrane material;
    releasing said tack from said insertion instrument; and
    withdrawing said insertion instrument.

11. The method of claim 10, wherein the insertion instrument comprises a core member and an outer sheath concentrically disposed about said core member.

12. The method of claim 11, wherein said loading step comprises engaging at least said enlarged proximal head of said tack component with said core member and receiving at least a portion of the tack component within said outer sheath.

* * * * *